United States Patent [19]

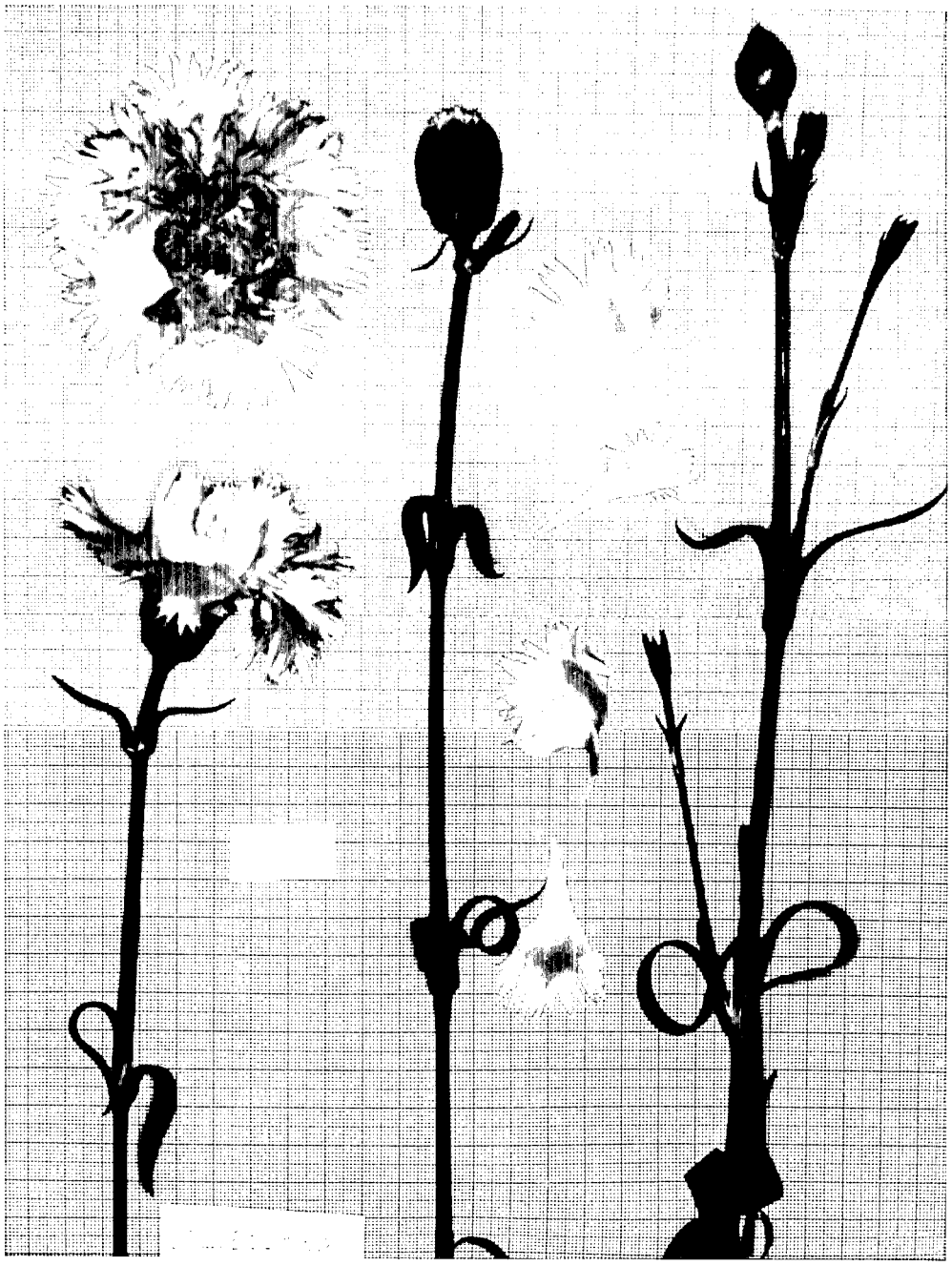

Nobbio

[11] Patent Number: Plant 5,762

[45] Date of Patent: Jul. 8, 1986

[54] CARNATION NAMED CASTELLARO

[76] Inventor: Giacomo Nobbio, Strada Villetta 5, San Remo, Imperia, Italy

[21] Appl. No.: 600,848

[22] Filed: Apr. 16, 1984

[51] Int. Cl.[4] ..... A01H 5/00
[52] U.S. Cl. ..... Plt./72
[58] Field of Search ..... Plt./70–73

*Primary Examiner*—James R. Feyrer

*Attorney, Agent, or Firm*—Charles W. Rummler

[57] ABSTRACT

A new carnation cultivar distinguished by its large cyclamen-pink flowers of the double type borne singly on long, slender stems of optimal elasticity, good endurance as a cut flower and suitability for shipment, and particularly well suited to commercial cultivation for the production of cut flowers under normal, protected growing conditions.

1 Drawing Figure

BACKGROUND OF THE NEW PLANT

This new carnation variety was originated in 1979 at my breeding establishment in San Remo, Italy, and resulted from my crossing an unnamed variety, identified in my records under U.S. Plant Pat. No. 9,113, as the seed parent, with the variety known as "Manon", as the pollen parent; the seed parent being of a cyclamen-pink color. The object of this crossing was to produce an improved red carnation variety with better cut flower endurance, particularly for commercial shipment. This objective is believed to have been accomplished in the products of this seedling. Reproduction of this seedling, by means of cuttings from the mother plant, was carried on under my direction at my propagation facilities in San Remo through many successive generations and this demonstrated conclusively that the novel characteristics of this new variety would hold true from generation to generation and appeared to be firmly fixed.

DESCRIPTION OF THE DRAWING

My new carnation cultivar is illustrated by the accompanying full color photographic drawing, which shows the inflorescence of a fully grown plant, the view including buds in various stages of opening, as well as a fully opened flower, together with specimens of the stems, both pinched and unpinched, and the flower petals, the color rendition being as nearly true as it is reasonably possible to obtain by means of conventional photographic procedures from specimens arranged as shown.

DESCRIPTION OF THE NEW PLANT

The following is a detailed description of my new carnation cultivar based upon observation of plants grown under conventional greenhouse procedure, the color designations being according to The R.H.S. Colour Chart published by The Royal Horticultural Society of London, England.

THE PLANT

Origin: Seedling.
Parentage:
- *Seed parent.*—An unnamed variety identified in my records as U.S. Plant Pat. No. 9,113.
- *Pollen parent.*—The variety known as "Manon".

Classification:
- *Botanic.*—*Dianthus caryophyllus.*
- *Commercial.*—Greenhouse carnation.

Form: Herbaceous bush with long stems having seven internodes visible immediately under the flower.
Growth: Vigorous and upright with slender stems of optimal elasticity.
Branching: Medium. The original shoot is pinched at about 10 or 12 cm. from the base, after reading a height of about 30 cm., tp produce 3 or 4 shoots or individual stems which grow rapidly and produce branches which form flower stems of considerable length. The individual stem growing from the base of the plant and any of its branches may be pruned according to the desired length of the stem for the terminal flower.
Foliage:
- *Quantity.*—Moderate or sparse on all flowering stems.
- *Leaf size.*—Medium.
- *Leaf shape.*—Linear, of medium length and breadth.
- *Texture.*—Smooth.
- *Color.*—Green.

THE BUD

Size: Medium.
Shape:
- *Before sepals divide.*—Ovoid.
- *As color appears.*—Cylindrical.

Sepals:
- *Condition.*—Upstanding.
- *Color.*—Inside adjacent the tips — A faint pink.

Calyx:
- *Size.*—Medium.
- *Shape.*—Bell-shaped.
- *Aspect.*—Smooth.

Outer calyx: Almost always formed from four bracts.
Stems: Slender and of optimum elasticity.
- *Length.*—Long.
- *Color.*—Medium green.

THE FLOWER

Blooming habit: Continuous.
Size of bloom: Large.
Type: Double.
Borne: Singly on long, upright stems.

Shape in full bloom: Symmetrical with cupule slightly flattened in center.

Petalage:

*Number of petals.*—From 40 to 80.

*Arrangement.*—Generally imbricated.

*Shape.*—Generally fan-shaped with incised margins.

*Color.*—Cardinal Red, R.H.S. 52B.

*Color distribution.*—Monochrome.

*Texture.*—Soft.

*Appearance.*—Velvety.

*Fragrance.*—Faint.

*Persistence.*—The petals hang on and dry.

Lasting quality: Good as a cut flower and with good stability for shipment.

REPRODUCTIVE ORGANS

Androecium: Absent during the winter period.

Stamens:

*Number.*—7 or 8.

*Anthers.*—Size: Normal. Color: White.

*Filaments.*—Length: 1.5 to 2 cm. Color: White.

*Pollen.*—Color: White.

Pistils:

*Number.*—2 to 4.

*Styles.*—Length: Medium. Color: Red.

*Stigma.*—Color: Pink.

Ovaries: Ribbed.

This new carnation variety is particularly distinguished from other commercially available varieties by its more brilliant chromatic hue and by the extraordinary shape of its petals, which features particularly distinguish the present variety from the known variety "San Giorgio" which the present variety most nearly resembles.

I claim:

1. A new and distinct carnation variety, substantially as herein shown and described, characterized by the bright red coloration of its blooms and the deeply incised margins of the flower petals, the flowers being of the double type and borne singly on slender, erect stems.

* * * * *

UNITED STATES PATENT AND TRADEMARK OFFICE

CERTIFICATE OF CORRECTION

PATENT NO. : Plant 5,762

DATED : July 8, 1986

INVENTOR(S) : Giacomo Nobbio

It is certified that error appears in the above-identified patent and that said Letters Patent are hereby corrected as shown below:

Column 1, line 6, delete "U.S. Plant Pat.".

Column 1, line 48, delete "U.S. Plant Pat.".

Signed and Sealed this

Twenty-first Day of October, 1986

[SEAL]

*Attest:*

DONALD J. QUIGG

*Attesting Officer* *Commissioner of Patents and Trademarks*